(12) United States Patent  
Bourget

(10) Patent No.: US 7,636,204 B1  
(45) Date of Patent: Dec. 22, 2009

(54) 360 DEGREE VIEW IMAGING SYSTEM

(75) Inventor: Paul L. Bourget, Kentwood, MI (US)

(73) Assignee: LumenFlow Corp., Middleville, MI (US)

( * ) Notice: Subject to any disclaimer, the term of this patent is extended or adjusted under 35 U.S.C. 154(b) by 72 days.

(21) Appl. No.: 11/928,731

(22) Filed: Oct. 30, 2007

(51) Int. Cl.  
G02B 17/00 (2006.01)  
G01N 21/00 (2006.01)  
G02B 13/06 (2006.01)

(52) U.S. Cl. .............. 359/726; 356/241.15; 356/241.5; 359/725

(58) Field of Classification Search ............... 73/152.01; 138/97; 348/84, 85; 356/241.1, 241.2, 241.3, 356/241.4, 241.5, 241.6; 359/725, 726  
See application file for complete search history.

(56) References Cited

U.S. PATENT DOCUMENTS

| 2,759,393 | A | * | 8/1956 | Mcleod | ...................... 356/138 |
| 3,221,593 | A | | 12/1965 | Ferris | |
| 3,551,061 | A | | 12/1970 | Glowa | |
| 3,610,763 | A | | 10/1971 | Mathews | |
| 3,724,922 | A | | 4/1973 | Jones | |
| 4,072,427 | A | | 2/1978 | Alsberg | |
| 4,135,824 | A | | 1/1979 | Jones | |
| 4,249,795 | A | | 2/1981 | Jones | |
| 4,373,811 | A | | 2/1983 | Jones | |
| 4,383,761 | A | | 5/1983 | Jones | |
| 4,429,957 | A | * | 2/1984 | King | ...................... 359/676 |
| 4,934,813 | A | | 6/1990 | Yaginuma et al. | |
| 5,543,972 | A | | 8/1996 | Kamewada | |
| 6,028,719 | A | | 2/2000 | Beckstead et al. | |
| 6,115,193 | A | * | 9/2000 | Shu | ...................... 359/725 |
| 6,784,447 | B2 | | 8/2004 | Gochar, Jr. | |
| 7,403,343 | B2 | * | 7/2008 | Togino | ...................... 359/725 |
| 2009/0082629 | A1 | * | 3/2009 | Dotan et al. | ............... 600/160 |

FOREIGN PATENT DOCUMENTS

| JP | 401015641 | 1/1989 |
| JP | 401015642 | 1/1989 |
| JP | 401097808 | 4/1989 |

* cited by examiner

Primary Examiner—David N Spector  
(74) Attorney, Agent, or Firm—Warner Norcross & Judd LLP

(57) ABSTRACT

A 360 degree view anamorphic resolution imaging system, which is a photonic device capable of illuminating the interior surface of a cylindrical object and then focusing the reflected light onto the detection surface of a viewing device. The system enables the selection of the level of image resolution from very high in the longitudinal axis near the center of the image, to moderate axial resolution near the outer edge of the image. The system may be used for viewing in-process machining operations, material flaw detection and measurement, and internal thread inspection.

7 Claims, 5 Drawing Sheets

Out of focus image in Region 11a

Sharp focus image in Region 11a

360 DEGREE VIEW IMAGING SYSTEM

BACKGROUND OF THE INVENTION

The present invention relates to 360 degree imagers for viewing the interior of a cylindrical surface or other area with limited access.

Conical surface reflector 360 degree imagers, sometimes referred to as panoramic viewing systems, are common in many industries where a continuous full view of the interior of a cylindrical surface is desired without the complication of moving optical or mechanical components. Exemplary applications for such imagers include pipe inspection, bore inspection and medical endoscopy.

The ability to resolve small features within a cylindrical interior requires a high resolution optical system. However, high resolution systems are typically difficult to implement because the radial positioning of the system is sensitive due to a limited depth of field. Typically, the solution is to compromise the resolution or to create a dedicated device that is matched to a specific internal diameter. Currently available borescopes typically are a compromise between the continuous full view of the interior of the cylindrical surface and the complexity of the supporting mechanisms.

SUMMARY OF THE INVENTION

The present invention is a conical surface reflector 360 degree imaging system (a) providing an anamorphic image resolution that allows the selection of a partial or whole image of an interior cylindrical surface and (b) enabling the projection of the image onto an image plane or detection device. The system includes a variable focusing mechanism providing variable radial depth of field to allow the system to be useable for a range of diameters.

The present invention reduces aberrations in the system by incorporating, either as a surface or as an additional component, a corrective element immediately adjacent or proximate to the conical surface reflector, thereby creating a compound conical surface reflector.

In the current embodiment, the system can be configured for variable depth of bores by projecting parallel or near parallel light from the output surface of the image magnifier lens sub system for transmission to the focus lens sub system.

The present invention provides a 360 degree view of the interior surface of a cylindrical object and projects that view as an anamorphic image on an image plane.

These and other objects, advantages and features of the invention will be more fully understood and appreciated by reference to the drawings and the description of the current embodiment.

DESCRIPTION OF THE CURRENT EMBODIMENT

Figure 1:
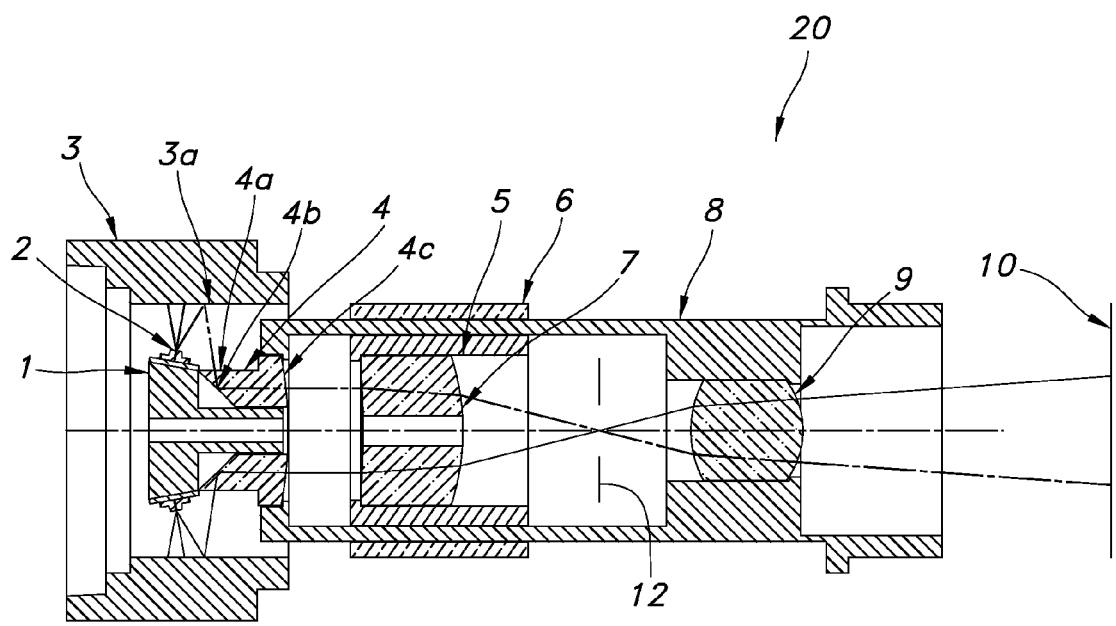
FIG. 1 is a cross-sectional view of the current embodiment of the 360 degree view anamorphic resolution imaging system.

An imaging device constructed in accordance with the current embodiment of the invention is illustrated in FIG. 1 and generally designated 20. The imaging device 20 is shown inserted into a cylindrical object 3 to be inspected. The imaging device 20 observes a 360 degree view of the interior surface 3a of the cylindrical object 3 and creates an anamorphic two-dimensional image of the view on the image plane 10.

As shown in FIG. 1, the imaging device 20 includes a compound conical surface reflector 4 which receives, reflects, and refracts 360 degree light about the system axis reflected by the cylindrical object interior surface 3a generated by the light emitting diode light source 2 to the image plane 10 via a series of lenses. The compound conical surface reflector 4 is in profile a symmetrical cylindrical solid capable of transmitting light through all exterior surfaces with the exception of the conical surface relief of reflective axicon surface 4b to which an optical mirror coating is applied.

A number of discrete light emitting diodes (LEDs) 2 are surface mounted on a flexible circuit and positioned on a mounting ring 1, and are aligned such that the light output of the LED devices will illuminate the interior surface 3a of the cylindrical object 3 so that the reflected light will be directed to the input surface 4a of the compound conical surface reflector 4. The light travels through the solid media of the compound conical surface reflector 4 and is reflected off the curved reflective axicon surface 4b toward the output surface 4c. The light is refracted at the output surface 4c and then travels through the image magnifier lens sub system 7, through the focus lens sub system 9, and is projected onto the image plane 10.

The system is essentially a microscope where the compound conical surface reflector 4 and the image magnifier lens sub system 7 operate as a variable objective. The focus lens sub system acts as the "eyepiece" of the system though it is designed for use with a camera plane. The system focus can be adjusted to compensate for variations in the inner diameter of the cylindrical object 3, thereby providing variable radial depth of field by repositioning the image magnifier lens sub system 7 along the central axis of the system mount 8.

The image magnifier lens sub system is secured within mounting tube 5 which is linked mechanically to the focus adjust interface 6 which provides a means of positioning the image magnifier lens sub system 7 within the system mount 8. The focus lens sub system 9 remains fixed within the system mount 8 in the current embodiment, although a moveable sub system that maintains a predetermined relationship with the image magnifier lens sub system 7 and the compound conical surface reflector 4 would be appropriate in an alternate embodiment. The compound conical surface reflector 4 is fixed mechanically at a predetermined distance from the image plane 10 depending upon the application. As shown in FIG. 1, for the current embodiment the mounting ring 1, the compound conical surface reflector 4, and the magnifier lens sub system 7 have a center bore for clearance to allow remote power to be applied to the LED light source 2. It is foreseeable that alternate embodiments will not require clearance bores and could be omitted.

Figure 2:
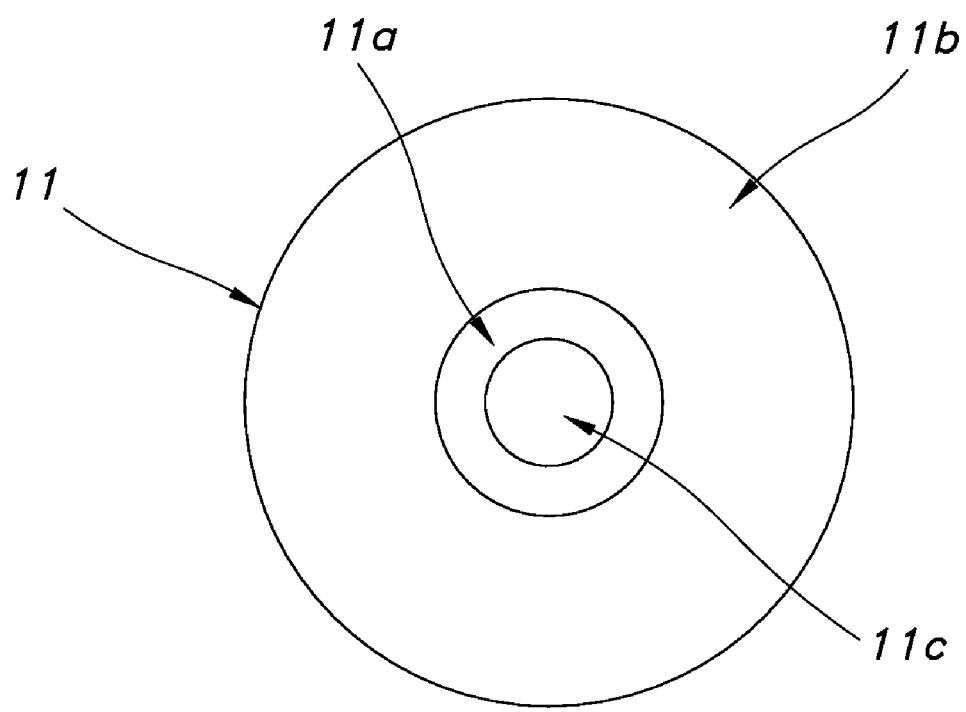
FIG. 2 is the anamorphic image projected on the image plane.
Figure 3:
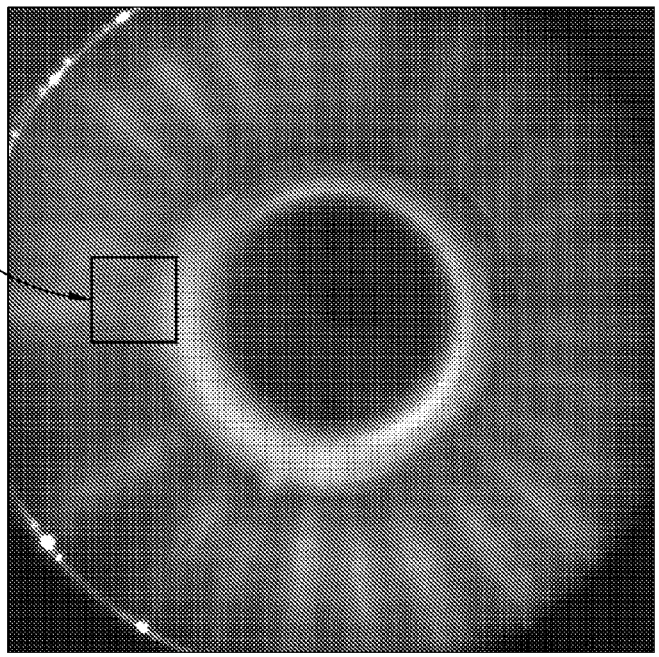
FIG. 3 is an image capture showing an out of focus condition.
Figure 4:
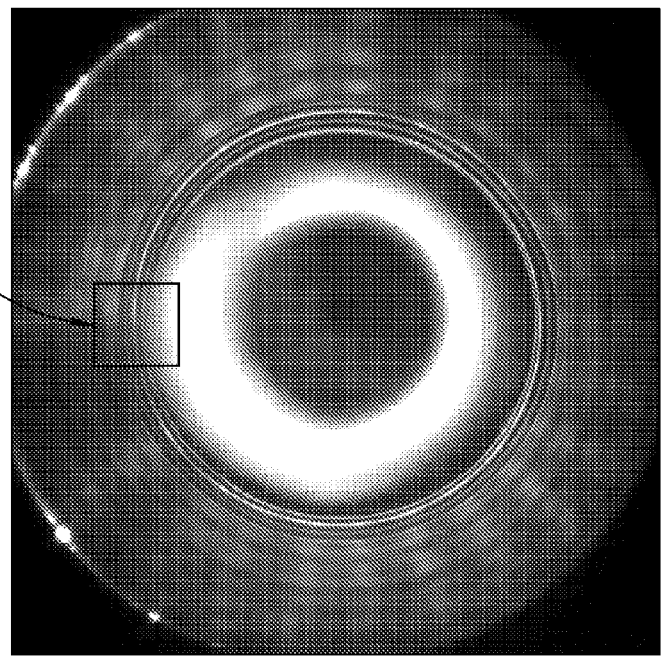
FIG. 4 is an image capture showing a sharp in focus condition.
Figure 5:
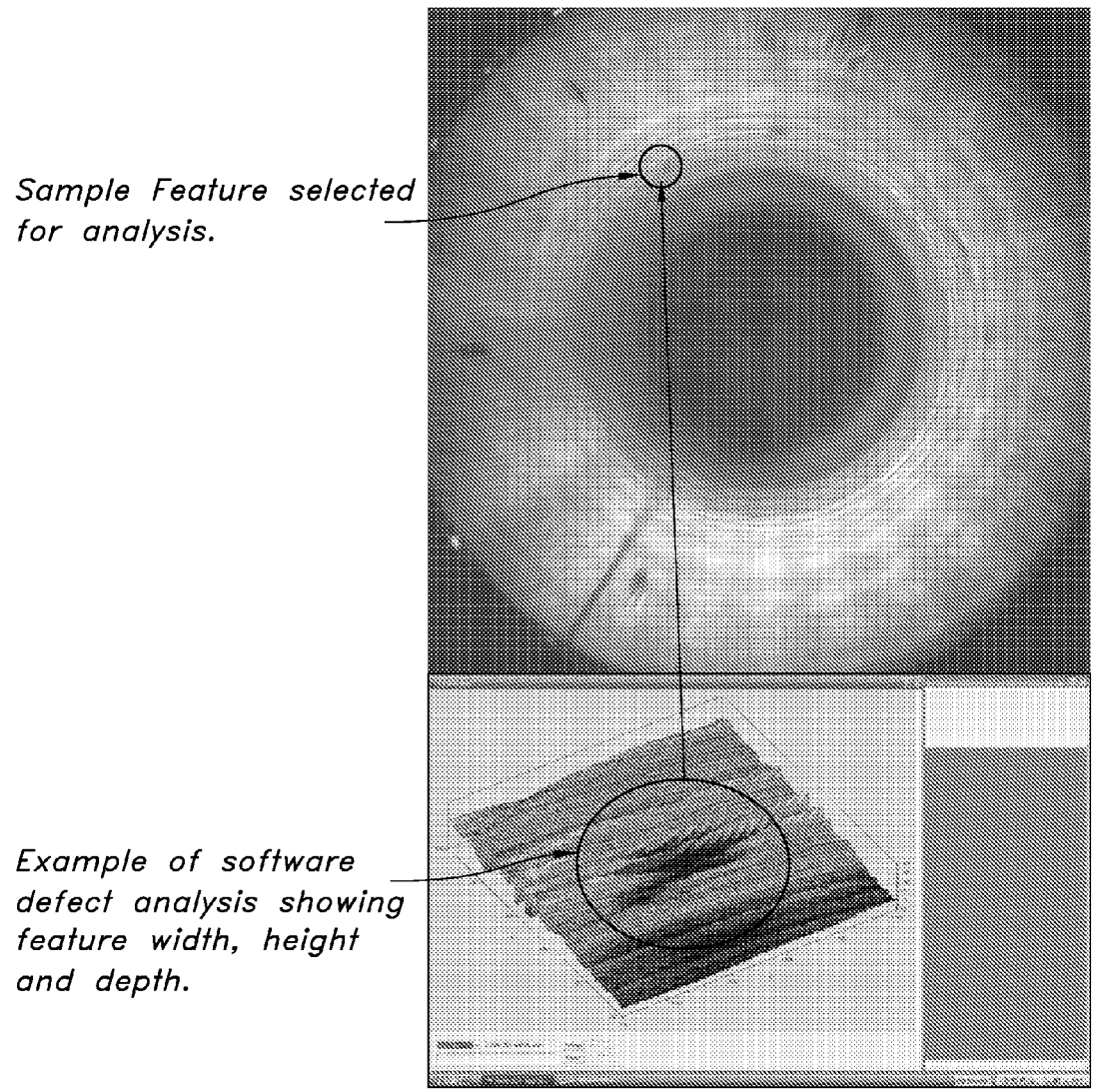
FIG. 5 is an image capture showing a sharp in focus condition with a feature selection and an example of defect analysis.
Figure 6:
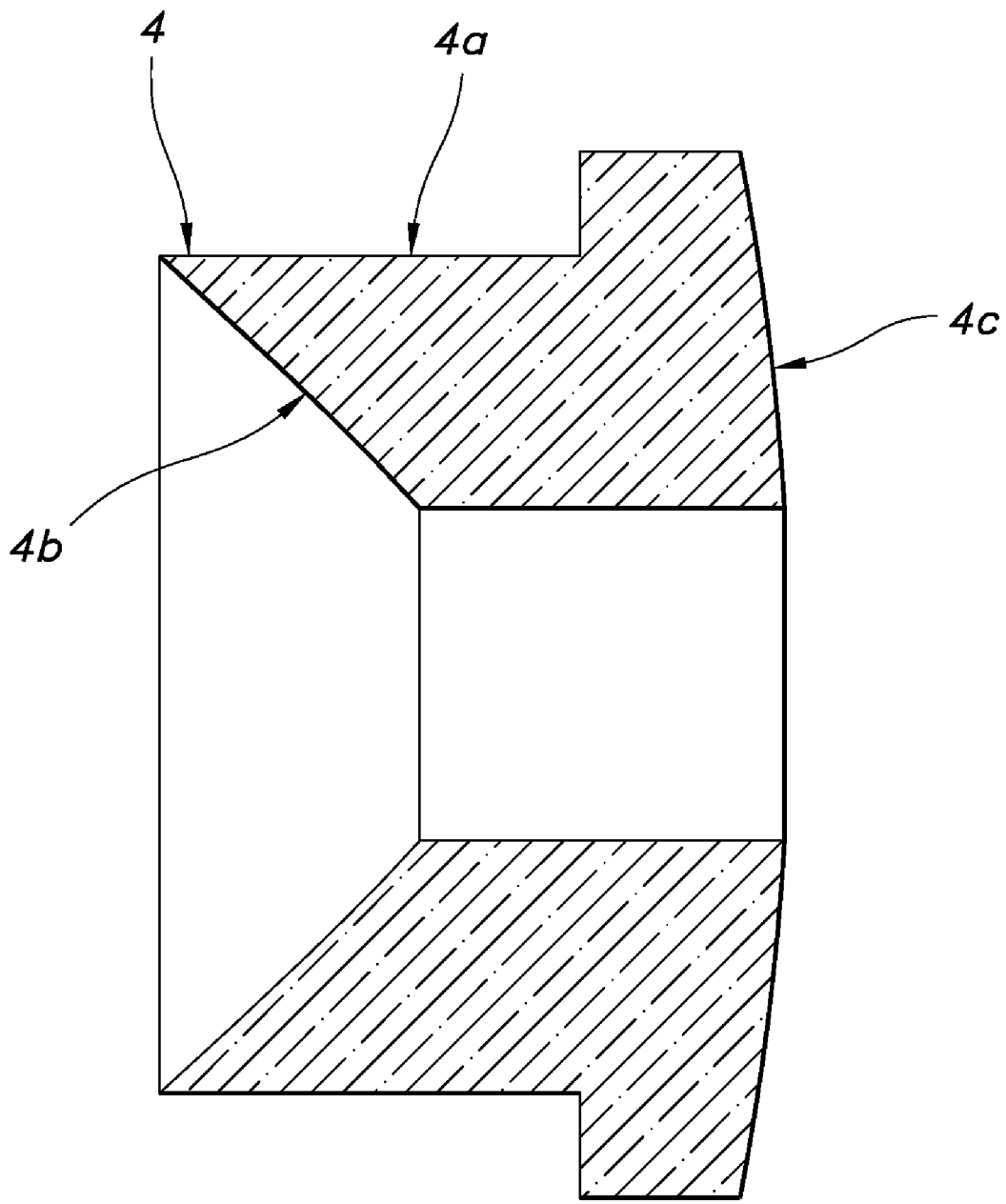
FIG. 6 is a cross-sectional view of the compound conical surface reflector.

FIG. 2 is a schematic illustration of the image of the interior surface 3a of the cylindrical object 3 as it would appear when projected on the image plane 10 as illustrated in reference FIG. 1. The interior surface 3a of the cylindrical object 3 is displayed as a continuous inverted image within the area defined as diameter 11. The image resolution will change in an anamorphic nonlinear fashion from very high resolution in the longitudinal axis in region 11a to moderate resolution in the radial axis in region 11b. The image in region 11c will appear as a dark, unfocused circle. It is considered that best system focus is achieved when the features of the interior surface 3a of the cylindrical object 3 form a sharp image within region 11a. FIG. 3 is an image capture from the device showing an out of focus condition. FIG. 4 is an image capture from the device showing a sharp in focus condition. When the best system focus is achieved, very high resolution images can be collected and processed as axial displacement measurement data. When combined with suitable software known to those skilled in the art (e.g. MaxIm DL software sold by Diffraction Limited), images gathered from any location within region 11a or region 11b can be used as measurement data and processed as three-dimensional features as shown in FIG. 5.

In the current embodiment, the input surface 4a of the compound conical surface reflector 4 is cylindrical (see FIG. 1). The diameter is specific to each application depending on the range of cylindrical object 3 diameters. It is foreseeable that alternate embodiments will benefit from input surfaces of differing profiles such as but not limited to a tapered cone or other conic surface.

The compound conical surface reflector 4 is unique in that the reflective axicon surface 4b and the output surface 4c are designed to be complimentary in such a way to magnify the image while reducing aberration. By combining the reflective axicon surface 4b with an optically active output surface 4c, a compound objective element is created. The compound objective in combination with the image magnifier lens sub system 7 provides a variable focus compound objective. In the current embodiment, image magnifier lens sub system 7 is an aplanatic triplet. This triplet, often found in microscope objectives, includes an achromatic doublet with an air-spaced positive meniscus. The meniscus side of the triplet faces the system stop 12, which is approximately halfway between the image magnifier lens sub system 7 and focus lens sub system 9. It is foreseeable that alternate embodiments may employ a more conventional "Cooke" triplet or a more complex "Heliar" lensing. The compound conical surface reflector 4 in combination with the image magnifier lens sub system 7 outputs light that is parallel—or nearly parallel—which allows the device to be scalable in such a way that minor changes in the optical path will allow the system to be used in a variety of applications, within a wide range of cylinder diameters, at a wide range of insertion depths, and a wide range of detector sizes.

When referencing the compound conical surface reflector 4 and the reflective axicon surface 4b, this application relies on the common and well established broad geometric definition of a conical surface, specifically a three-dimensional surface formed by sweeping a line about an axis of symmetry. The line may be any type of line, specifically including linear or nonlinear lines.

In the current embodiment, the reflective axicon surface 4b profile of the compound conical surface reflector 4 is formed by a hyperbolic function. The formula for the curvature is specific to each application depending on desired magnification, cylinder diameter, and allowable aberration and distortion. The primary determining factor for selecting a hyperbolic function is the desire to minimize coma error which is accomplished by varying the conic constant K. The eccentricity e of the conic section is defined by the equation $K=-e^2$.

It is foreseeable that alternate embodiments will require mirrored surfaces of differing profiles within the common geometric definition of a conical surface such as but not limited to elliptic or parabolic functions.

In the current embodiment, the output surface 4c has a simple radius integral to the compound conical surface reflector 4. The addition of a curvature to the output surface 4c is necessary to minimize astigmatism. It is foreseeable that alternate embodiments will require output surfaces of differing geometries such as but not limited to planar, aspherical, or toroidal. It is also foreseeable that alternate embodiments will require that the compound conical surface reflector 4 and the output surface 4c will be separate and distinct elements depending on the application.

For the current embodiment, the first level approximation of the optical system is summarized as follows:

1. The optical system, including the image magnifier lens sub system 7 and the focus lens sub system 9, is designed to establish the preliminary system resolution. The linear optical system is optimized for the required resolution with consideration given to the cylindrical object interior surface 3a diameter, the image plane 10, and the image size to be projected onto the image plane 10.
2. The reflective axicon surface 4b of the compound conical surface reflector 4 is inserted into the system and optimized to minimize coma error by varying the conic constant K. In the current embodiment, the conic constant K is −1.75 with a resultant Seidel coefficient coma error of 0.00034. As long as these two parameters are held in relationship to each other, it is possible to choose the focal lengths for image magnifier lens sub system 7 and focus lens sub system 9 for a range of diameters of cylindrical object 3.
3. The output surface 4c of the compound conical surface reflector 4 is inserted into the system to reduce astigmatism. This is done with a simple spherical surface, which is a first level approximation of a toroidal surface but is easier to manufacture.
4. Further refinement of the system is required when consideration is given to the input surface 4a.
5. The reflective axicon surface 4b of the compound conical surface reflector 4 can then be modified to effect system magnification by varying the Radius.

In the current embodiment, the focus lens sub system 9 is a "Tessar" lens system. It will be recognized by those skilled in the art that the focus lens sub system 9 may be implemented using a plurality of lenses, such as a "Hektor anastigmat" or a "Double Gauss", in order to perform within the total system as described, and such implementations are considered within the scope of the present invention. It will be further recognized by those skilled in the art that in order to increase the range of diameters of the cylindrical object interior surface 3a, it would be appropriate to change the optical power of focus lens sub system 9. This can be achieved by changing either or both of its focal length or its spatial relationship to the image magnifier lens sub system 7.

The image plane 10 of the current embodiment is a CCD camera, but can be any suitable device configured to accept an image.

The above description is that of the current embodiment of the invention. Various alterations and changes can be made without departing from the spirit and broader aspects of the invention as set forth in the following claims, which are to be interpreted in accordance with the principles of patent law including the Doctrine of Equivalents.

The embodiments of the invention in which an exclusive property or privilege is claimed are defined as follows:

1. A 360 degree imaging system comprising:
a reflector lens system including a cylindrical input surface, a reflective axicon surface, and an optically active output surface, the reflective surface and the output surface being complimentary to magnify an image and to reduce aberration, the reflector lens system capable of receiving radial light through the input surface from a curved object and reflecting the radial light from the axicon surface in a generally axial direction through the output surface;
a magnifier lens system;
a system stop; and
a focus lens system, the three systems and the system stop being optically aligned in the order of the reflector lens system, the magnifier lens system, the system stop, and the magnifier lens system, the reflector lens system and the focus lens system being fixed relative one another, the magnifier lens system and the focus lens system being movable relative one another.

2. An imaging system as defined in claim 1 wherein the three lens systems are selected to produce a flat image from a curved object field.

3. An imaging system as defined in claim 1 wherein the output surface is spherical.

4. A 360 degree imaging system comprising:
a cylindrical objective lens system including an input surface, a reflector surface, and an output surface, the reflector surface being an axicon;
a magnifier lens system;
a system stop; and
a focus lens system, the objective lens system and the focus lens system being fixed relative one another, the magnifier lens system and the focus lens system being movable relative one another enabling the depth of field to be adjusted, the lens systems together creating a flat image from a curved object field.

5. A 360 degree imaging system as defined in claim 1 wherein the cylindrical input surface, the reflective axicon surface, the output surface, and the magnifier lens system operate as a variable objective.

6. A 360 degree imaging system as defined in claim 1 wherein the magnifier lens assembly comprises one of an aplanatic triplet, a Cooke triplet, and a Heliar lens.

7. A 360 degree imaging system as defined in claim 1 wherein the focus lens system comprises one of a Tessar lens system, a Hektor anastigmat, and a Double Gauss.

* * * * *